(12) United States Patent
Ohtani

(10) Patent No.: US 6,839,640 B2
(45) Date of Patent: Jan. 4, 2005

(54) METHOD AND APPARATUS FOR DIAGNOSING DAMAGES OF CONDUCTIVE MATERIALS

(75) Inventor: Toshihiro Ohtani, Kanagawa (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 10/098,171

(22) Filed: Mar. 15, 2002

(65) Prior Publication Data

US 2003/0167137 A1 Sep. 4, 2003

(30) Foreign Application Priority Data

Mar. 4, 2002 (JP) ........................................ 2002-057270

(51) Int. Cl.⁷ .............................................. G01B 5/30
(52) U.S. Cl. ....................................................... 702/35
(58) Field of Search .......................... 702/35, 39, 103, 702/104, 171; 73/598, 599, 627, 632

(56) References Cited

U.S. PATENT DOCUMENTS

| 4,777,824 A | 10/1988 | Alers et al. ................... 73/643 |
| 5,808,202 A | 9/1998 | Passarelli, Jr. ................ 73/643 |
| 6,038,925 A | 3/2000 | Ohtani et al. ................. 73/598 |
| 6,109,108 A | 8/2000 | Ohtani et al. ................. 73/599 |

FOREIGN PATENT DOCUMENTS

| DE | 26 57 957 | 6/1978 |
| DE | 39 04 440 A1 | 8/1990 |
| EP | 0 458 425 A2 | 11/1991 |
| GB | 2 006 433 A | 5/1979 |
| JP | 3052049 | 6/1997 |
| JP | 3052050 | 6/1997 |
| JP | 9-257760 | 10/1997 |

OTHER PUBLICATIONS

M. Hirao et al., "Ultrasonic Attenuation Peak During Fatigue of Polycrystalline Copper," in *ACTA MATER.* 48, pp. 517–524 (2000).

*Primary Examiner*—Michael Nghiem
(74) *Attorney, Agent, or Firm*—Westerman, Hattori, Daniels & Adrian, LLP (57) ABSTRACT

A diagnosing method and apparatus non-destructively performing damage evaluation of a piled up structure of conductive materials by using acoustic waves. The diagnosing method according to the present invention includes the steps of placing an electro-magnetic acoustic transducer 20 out of contact with a piled up structure 34 of conductive materials 32 and 34 piled up with a non-conductive interface 33 (35) interposed therebetween, transmitting ultrasonic waves from one side 31 of the piled up structure by the electro-magnetic acoustic transducer 20, receiving ultrasonic waves reflected from the other side of the piled up structure, and diagnosing a damaged condition of the piled up structure on the basis of the ultrasonic velocity and attenuation of the received ultrasonic waves.

5 Claims, 9 Drawing Sheets

| MODE | RESONANCE FREQUENCY | |
|---|---|---|
| | FIRST LAYER | SECOND LAYER |
| 1 | 0.79 | 0.31 |
| 2 | 1.57 | 0.63 |
| 3 | 2.36 | 0.94 |
| 4 | 3.14 | 1.26 |
| 5 | 3.93 | 1.57 |
| 6 | 4.71 | 1.88 |
| 7 | 5.50 | 2.20 |
| 8 | 6.28 | 2.51 |
| 9 | 7.07 | 2.83 |
| 10 | 7.85 | 3.14 |
| 11 | 8.64 | 3.45 |
| 12 | 9.42 | 3.77 |
| 13 | 10.21 | 4.08 |
| 14 | 10.99 | 4.40 |
| 15 | 11.78 | 4.71 |

Fig. 9

METHOD AND APPARATUS FOR DIAGNOSING DAMAGES OF CONDUCTIVE MATERIALS

BACKGROUND OF THE INVENTION

The present invention relates to a method and apparatus for diagnosing damage to electrically conductive materials, e.g. corrosion or fatigue, by using an ultrasonic resonance method. With the ultrasonic resonance method, ultrasonic waves are transmitted and received through a conductive material by an EMAT (Electro-Magnetic Acoustic Transducer) disposed adjacent to the surface of the conductive material. More specifically, the present invention relates to a method and apparatus for diagnosing by using an EMAT a damaged condition, e.g. corrosion, creep, stress-corrosion crack, or fatigue, of a piled up or laminated structure of conductive materials fastened together with rivets, bolts or the like.

Figure 1:
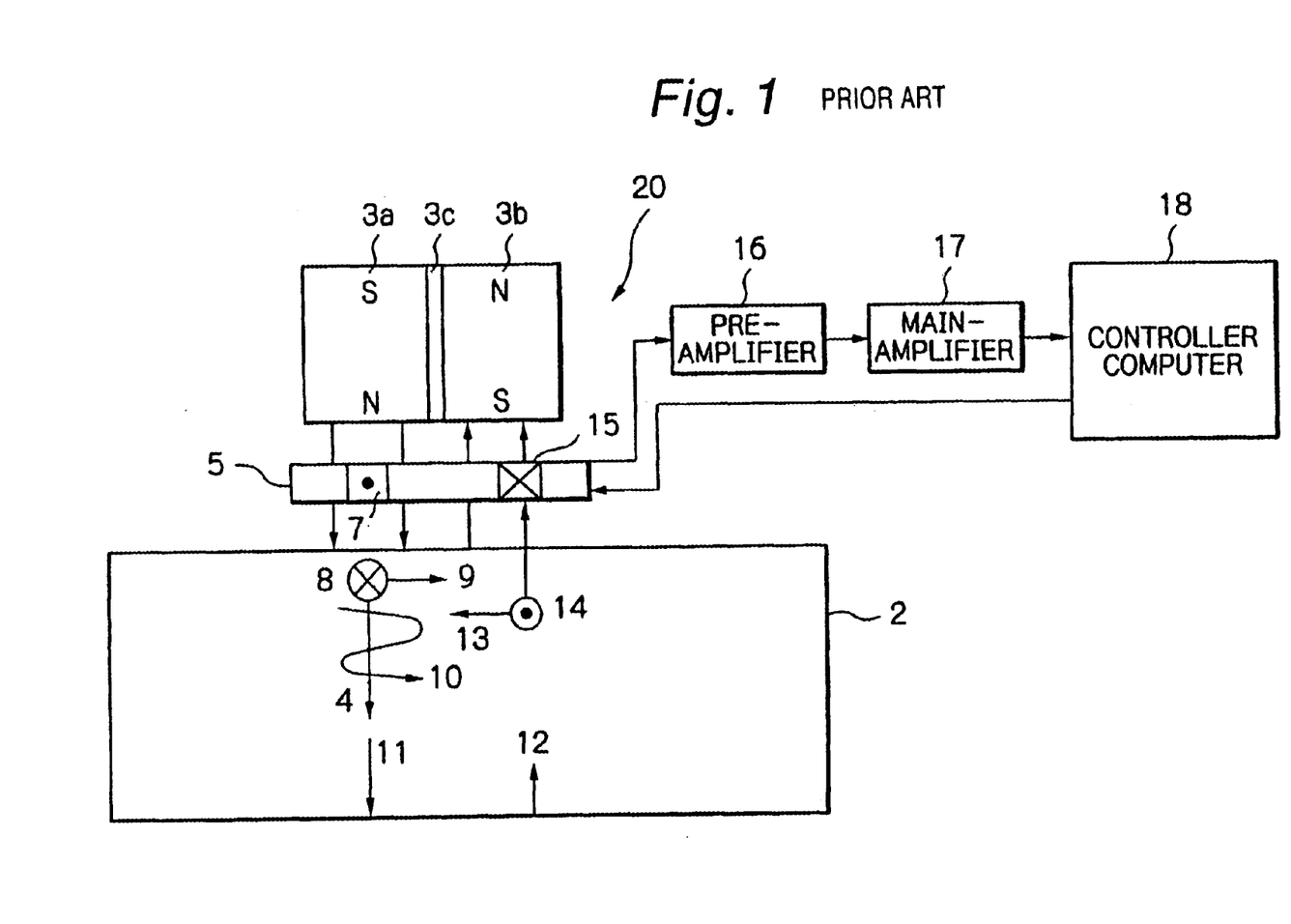
FIG. 1 is a diagram for explaining the principle of a publicly known electro-magnetic acoustic transducer (EMAT) 20.

Electro-magnetic acoustic transducers (EMATs) have been disclosed, for example, in the Gazette of Japanese Patent No. 3052049 and the Gazette of Japanese Patent No. 3052050. FIG. 1 is a diagram for explaining the principle of a publicly known electro-magnetic acoustic transducer (EMAT). As shown in FIG. 1, the EMAT 20 includes a pair of permanent magnets 3a and 3b disposed adjacent to the upper surface of a conductive material (object to be measured) 2. The EMAT 20 further includes a driver coil 5 and a detection coil 15. The pair of permanent magnets 3a and 3b are placed adjacent to each other with a spacer 3c interposed therebetween. The permanent magnets 3a and 3b generate magnetic fields opposite in direction to each other with respect to the conductive material 2. The permanent magnets 3a and 3b may be electromagnets arranged to generate similar magnetic fields. The driver coil 5 and the detection coil 15 are flat plate-shaped coils, which are disposed between the permanent magnets 3a and 3b on the one hand and the upper surface of the conductive material 2 on the other. The conductive material (object to be measured) 2 may be covered with a non-conductive material because the EMAT can transmit and receive ultrasonic waves in a non-contact manner.

The permanent magnets 3a and 3b form a static magnetic field 4 in the thickness direction of the conductive material 2. When the driver coil 5 is supplied with a radio-frequency burst current 7 from a controller 18, an eddy current 8 is generated on the surface of the conductive material 2 in the direction reverse to that of the current 7. The eddy current 8 and the static magnetic field 4 interact each other to generate a Lorentz force 9 according to the Fleming's left-hand rule. The Lorentz force 9 acts on free electrons in the conductive material 2, causing the free electrons to collide with ions and so forth, thereby inducing motions in a direction perpendicular to the directions of the static magnetic field 4 and the radio-frequency current 7 inside the conductive material 2, and thus generating ultrasonic shear waves 10.

The ultrasonic shear waves 10 travel in the direction of the arrow 11 in FIG. 1. The ultrasonic shear waves 10 are reflected by the upper or lower surface of the conductive material 2 and also reflected by flaws, defects, grain boundaries, changes of material's structure, etc. in the conductive material 2 to travel in the direction of the arrow 12. When the reflected ultrasonic shear waves 10 reach the vicinity of the upper surface of the conductive material 2, a force 13 is generated. The force 13 and the static magnetic field 4 interact each other to generate an eddy current 14. The eddy current 14 is detected with the detection coil 15. The detected current is amplified by a pre-amplifier 16 and a main amplifier 17 and sent to the controller 18. The controller 18 analyzes the current received from the main amplifier 17 to evaluate flaws, defects, grain boundaries, changes of material's structure, etc. in the conductive material 2.

The gazette of Japanese Patent No. 3052049 discloses an electro-magnetic acoustic transducer in which a transmission coil for generating ultrasonic waves and a reception coil for detecting ultrasonic waves are each formed into a spiral elongated shape and disposed to overlie one another with an insulating sheet interposed therebetween, and a grounded portion common to the two coils is formed to extend through a through-hole in the insulating sheet, thereby making the coil unit compact in size.

The gazette of Japanese Patent No. 3052050 discloses an electro-magnetic acoustic transducer in which a transmission coil for generating ultrasonic waves and a reception coil for detecting ultrasonic waves are formed into a meandering shape and disposed to overlie one another with an insulating sheet interposed therebetween, and grounded portions of the coils are connected in common through a through-hole in the insulating sheet, thereby making the coil unit compact in size and allowing diagnosis of flaws, defects, grain boundaries, changes of material's structure, etc. in a cylindrical conductive material 2.

SUMMARY OF THE INVENTION

The conventional non-destructive method of diagnosing a conductive material using an electro-magnetic acoustic transducer is applicable to a case where an object to be diagnosed is a monolithic conductive material through which ultrasonic waves can pass, but incapable of evaluating a piled up structure comprising a plurality of piled up layers of conductive materials. That is, the conventional diagnosing method using an electro-magnetic acoustic transducer is capable of evaluating the uppermost layer of a piled up structure but incapable of diagnosing or evaluating the second layer, the third layer and so forth, which are disposed successively below the uppermost layer. A first object of the present invention is to provide a diagnosing method and apparatus capable of evaluating flaws, defects, grain boundaries, changes of material's structure, etc. in each of the second and following layers of a piled up structure from above the surface of the first layer of a conductive material in a non-contact manner by using an electro-magnetic acoustic transducer (EMAT).

Another object of the present invention is to provide a diagnosing method and apparatus capable of evaluating fatigue, creep, corrosion, stress crack, etc. in all or each of the layers of a piled up structure of conductive materials by using an electro-magnetic acoustic transducer without the need to disassemble the piled up structure and before the conductive material becomes cracked. A further object of the present invention is to provide a method and apparatus allowing diagnosis of damage to fasteners, e.g. rivets or bolts, used to fasten together a plurality of layers of conductive material, or of a reduction in fastening force of such fasteners without the need to disassemble the piled up structure.

A still further object of the present invention is to provide a method and apparatus capable of diagnosing ultrasonic signals that allow diagnosis or evaluation of all or each of the layers of a piled up structure of conductive materials at a place away from the piled up structure and an electro-magnetic acoustic transducer by using predetermined software. A still further object of the present invention is to provide a method and apparatus whereby ultrasonic signals containing information concerning, for example, damage to each layer of a piled up structure, e.g. an airplane or a bridge, fastened with fasteners, e.g. rivets or bolts, or damage to such fasteners are taken out without disassembling the piled up structure, and the signals taken out are processed at somewhere else or at a remote place, thereby allowing such damage to be evaluated and diagnosed accurately in a short period of time. Other objects and advantages of the present invention will become apparent from the following description and the drawings.

A diagnosing method according to the present invention diagnoses a damaged condition of a piled up structure of conductive materials piled up with a non-conductive interface interposed therebetween. The method according to the present invention includes the steps of placing an electro-magnetic acoustic transducer out of contact with the piled up structure, transmitting ultrasonic waves capable of propagating through the non-conductive interface from one side of the piled up structure by the electro-magnetic acoustic transducer, receiving ultrasonic waves reflected from the other side of the piled up structure by the electro-magnetic acoustic transducer, and diagnosing the damaged condition of the piled up structure on the basis of changes in the ultrasonic velocity and attenuation of the received ultrasonic waves.

In the method according to the present invention, the electro-magnetic acoustic transducer transmits ultrasonic waves of a resonant frequency common to the plurality of layers of conductive materials piled up with a non-conductive interface interposed therebetween. The step of diagnosing the damaged condition includes the step of diagnosing the damaged condition of the whole of the piled up structure in the thickness direction thereof. The method according to the present invention further includes the steps of transmitting ultrasonic waves reflectible by the non-conductive interface from one side of the piled up structure, and comparing the condition of the ultrasonic waves passing through the non-conductive interface and reflected from the other side and the condition of the ultrasonic waves reflected by the non-conductive interface to diagnose a damaged condition for each layer of the piled up structure.

A diagnosing method according to the present invention diagnoses the condition of a piled up structure of conductive materials piled up with a non-conductive interface interposed therebetween and fastened together with a fastening member. The method according to the present invention includes the steps of placing an electro-magnetic acoustic transducer out of contact with the piled up structure, transmitting ultrasonic waves capable of propagating through the non-conductive interface from one side of the piled up structure by the electro-magnetic acoustic transducer, receiving ultrasonic waves reflected from the other side of the piled up structure by the electro-magnetic acoustic transducer, and diagnosing fastening force of the fastening member of the piled up structure on the basis of changes in the ultrasonic velocity and attenuation of the received ultrasonic waves. The diagnosing step is carried out by using computer software. Further, the diagnosing step includes the step of transmitting an electric signal to a place separate or remote from a part of the piled up structure to be diagnosed.

An apparatus according to the present invention diagnoses a damaged condition of a piled up structure of conductive materials piled up with a non-conductive interface interposed therebetween. The apparatus according to the present invention includes an electro-magnetic acoustic transducer placed out of contact with the piled up structure, a controller for controlling the operation of the electro-magnetic acoustic transducer, and a computer for evaluating damage to the piled up structure on the basis of an electric signal obtained by the electro-magnetic acoustic transducer. The electro-magnetic acoustic transducer can transmit ultrasonic waves of a frequency capable of propagating through the non-conductive interface from one side of the piled up structure and can also receive ultrasonic waves reflected from the other side of the piled up structure. The computer diagnoses the damaged condition of the piled up structure on the basis of the ultrasonic velocity and attenuation of the received ultrasonic waves.

An apparatus according to the present invention diagnoses the condition of a piled up structure of conductive materials piled up with a non-conductive interface interposed therebetween and fastened together with a fastening member. The apparatus according to the present invention includes an electro-magnetic acoustic transducer placed out of contact with the piled up structure, a controller for controlling the operation of the electro-magnetic acoustic transducer, and a computer for evaluating damage to the piled up structure on the basis of an electric signal obtained by the electro-magnetic acoustic transducer. The electro-magnetic acoustic transducer can transmit ultrasonic waves of a frequency capable of propagating through the non-conductive interface from one side of the piled up structure and can also receive ultrasonic waves reflected from the other side of the piled up structure. The computer diagnoses fastening force of the fastening member of the piled up structure on the basis of the ultrasonic velocity and attenuation of the received ultrasonic waves.

The apparatus according to the present invention further includes a communication mechanism capable of teletransmission. The communication mechanism can transmit the electric signal obtained by the electro-magnetic acoustic transducer to the computer having diagnosing software. It is preferable in the method and apparatus according to the present invention that the computer should previously be stored with a reference measured value of a damage-free piled up structure as a reference value, and a diagnosis should be made by comparing a measured value of a piled up structure to be measured with the reference measured value.

BRIEF DESCRIPTION OF THE DRAWINGS

FIG. 7a is a diagram showing the arrangement of a testing apparatus for examining the fatigue of a material and changes in the attenuation coefficient and velocity of ultrasonic waves, which is used in the evaluation method of the present invention, and FIG. 7b is a graph of the changes in the attenuation coefficient and velocity obtained by using the testing apparatus shown in FIG. 7a.

FIG. 8a is a diagram showing the arrangement of a testing apparatus for examining the fatigue of a material and changes in the attenuation coefficient and velocity of ultrasonic waves, which is used in the evaluation method of the present invention, and FIG. 8b is a graph of the changes in the attenuation coefficient and velocity obtained by using the testing apparatus shown in FIG. 8a.

EXPLANATION OF REFERENCE NUMERALS

2: conductive material; 3a, 3b: permanent magnets; 4: static magnetic field; 5: driver coil; 7: radio-frequency current; 8: eddy current; 9: Lorentz force; 10: ultrasonic waves (shear waves); 17: main amplifier; 18: controller; 20: electro-magnetic acoustic transducer (EMAT); 32: first layer; 34: piled up structure; 36: second layer; 38: rivet; 22: telecommunication mechanism.

DETAILED DESCRIPTION OF THE EMBODIMENT

Figure 2:
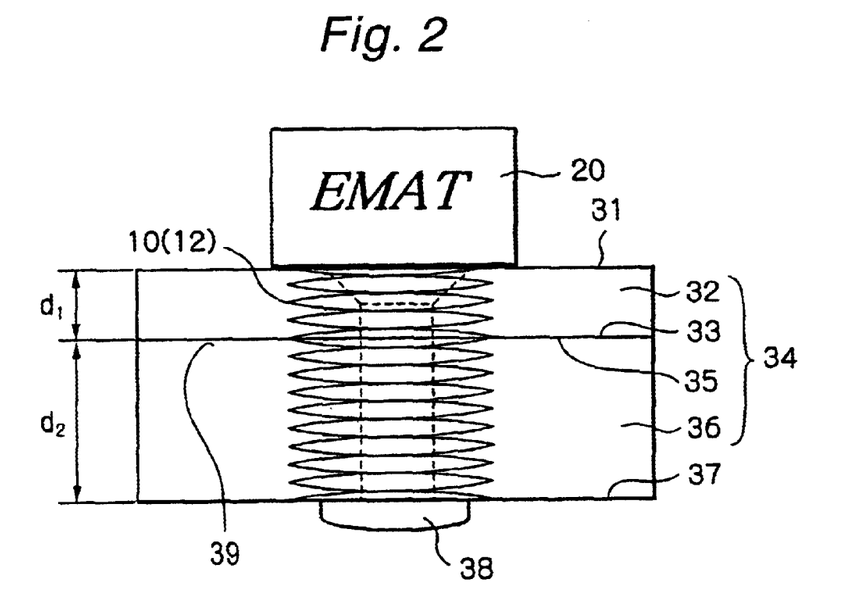
FIG. 2 is a diagram showing the principle of the present invention.

FIG. 2 is a diagram showing the principle of the present invention. In FIG. 2, an object to be diagnosed is a piled up structure 34 comprising a first layer 32 of a conductive material and a second layer 36 of a conductive material that are fastened together with a rivet 38. An electro-magnetic acoustic transducer EMAT 20 is disposed adjacent to the upper surface 31 of the piled up structure 34. The EMAT 20 has a pair of permanent magnets, together with a driver coil and a detection coil, in the same way as shown in FIG. 1. The EMAT 20 is positioned so that all ultrasonic waves generated by the EMAT 20 will not pass through the rivet 38. The uppermost surface 31 of the piled up structure 34 may be covered with a non-conductive material, e.g. paint, because the EMAT 20 can generate ultrasonic waves in the structure in a non-contact manner.

When a radio-frequency current is supplied to the driver coil of the EMAT 20, ultrasonic waves 10 are generated in the first layer 32 as in the case of FIG. 1. The ultrasonic waves 10 generated in the first layer 32 are reflected by an end surface 33 of the first layer 32 or by an end surface 37 of the second layer 36, and the reflected ultrasonic waves 12 are detected by the detection coil of the EMAT 20.

If the frequency of the current supplied to the driver coil of the EMAT 20 is swept, a spectrum of resonance caused in the thickness direction of the piled up structure 34 is obtained according to equation (1).

$$fn = nV/(2d) \quad (1)$$

where fn: the resonant frequency n: the resonant mode

V: the ultrasonic velocity d: the plate thickness.

In the resonant spectrum obtained according to equation (1), a curve fitting is performed near a resonant frequency with a Lorentz function or a Gaussian function. The center frequency is determined as a resonant frequency, and the EMAT 20 is driven at the resonant frequency to obtain an attenuation curve. The following exponential function (2) is fitted to the obtained attenuation curve, and the time constant in equation (2) is determined as the attenuation coefficient α.

$$A = A0 \exp\{-\alpha(t-t0)\} \quad (2)$$

When the thickness d1 of the first layer 32 of the piled up structure 34 and the thickness d2 of the second layer 36 are different from each other, the ultrasonic waves 10 propagate into the second layer 36 only when the resonant mode forms a loop at the-interface the interface 39(between the end surface 33 of the first layer 32 and the upper surface 35 of the second layer 36). The frequency fn in that case can be obtained if the ultrasonic velocity V and the plate thickness d1 in equation (1) are known.

It is possible to obtain information containing damage information concerning both the first layer 32 and the second layer 36 by obtaining the ultrasonic velocity V and the attenuation coefficient α in equation (2) at the frequency fn at which the ultrasonic waves 10 propagate into the second layer 36. In a mode that does not form a loop at the interface, i.e. at a frequency other than the frequency fn, information obtained contains only damage information concerning the first layer 32. Therefore, information containing only damage information concerning the second layer 36 can be obtained by subtracting the information containing only damage information concerning the first layer 32 from the information containing damage information concerning both the first layer 32 and the second layer 36.

When the fastening force of the rivet or bolt decreases owing to damage, bonding power at the interface weakens, so that the transmission of the ultrasonic waves from the upper layer to the lower layer is degraded. Consequently, there is no leakage of energy to the lower layer, and the ultrasonic signal is intensified. This causes an increase in the amplitude of the resonant frequency or a reduction in the attenuation coefficient. Therefore, the fastening force of the rivet or bolt can be diagnosed by examining the increase in the amplitude of the resonant frequency or the reduction in the attenuation coefficient.

Conventionally, an eddy current testing method or a contact type ultrasonic method is used to evaluate damage after the occurrence of a crack. A low-frequency eddy current testing method is used for a crack in the second and following layers of a piled up structure. However, the crack detection sensitivity of the conventional method is not less than 5 mm. Further, the crack detection requires a measurer skilled in technique. The method according to the present invention allows non-contact diagnosis of damage to a piled up structure from the uppermost surface thereof and permits damage diagnosis for the whole structure in the thickness direction or damage diagnosis for each layer without the need to disassemble the piled up structure. In addition, the method according to the present invention allows diagnosis of a reduction in the fastening force of rivets, bolts, etc. of the piled up structure to be made in a short period of time and without the need of special skill.

Figure 3:
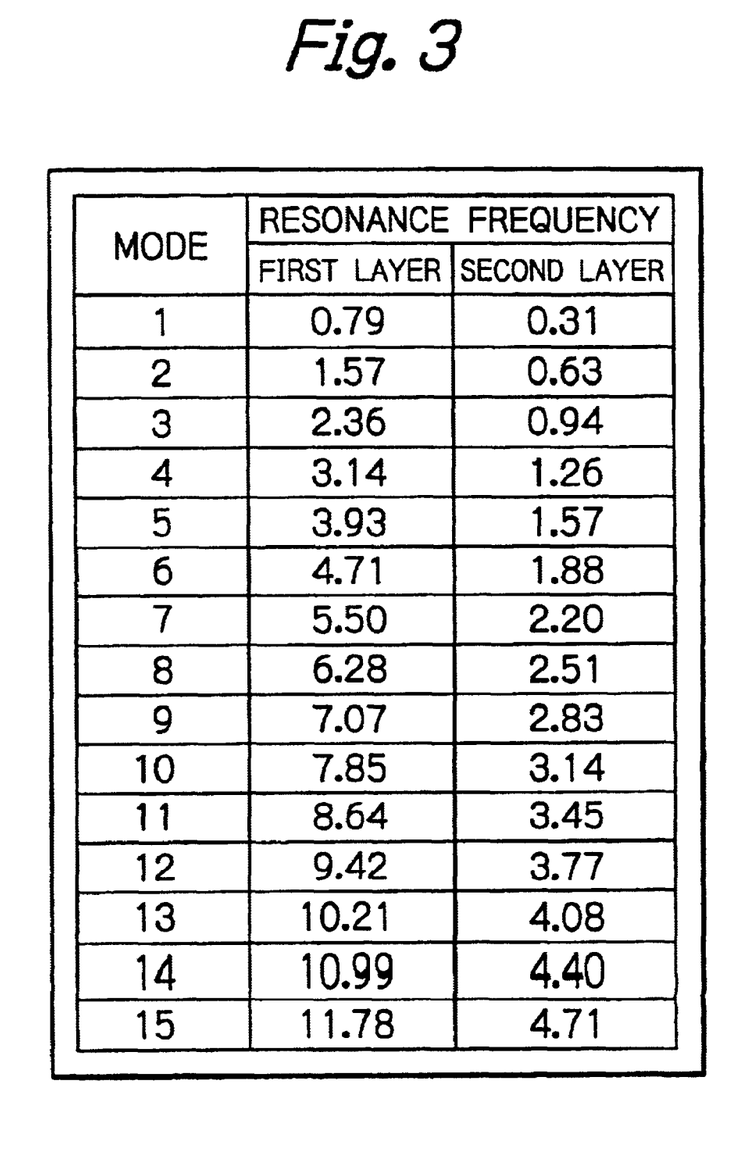
FIG. 3 is a table showing the 1 st to 15 th resonant frequencies fn in a first layer and a second layer.

FIG. 3 is a table showing the 1 st to 15 th resonant frequencies fn in a first layer 32 of a conductive material with a thickness d1 of 2 mm and a second layer 36 of a conductive material with a thickness d2 of 5 mm. According to FIG. 3, the 2 nd resonant frequency for d1 and the 5 th resonant frequency for d2 are the same, i.e. 1.57 MHz. Therefore, there is a possibility that information containing damage information concerning both the first and second layers will be obtainable by using ultrasonic waves of this frequency. Further, according to FIG. 3, the 4 th resonant frequency for d1 and the 10 th resonant frequency for d2 are the same, i.e. 3.14 MHz, and the 6 th resonant frequency for d1 and the 15 th resonant frequency for d2 are the same, i.e. 4.71 MHz. Therefore, there is a possibility that information containing damage information concerning both the first and second layers will be obtainable by using ultrasonic waves of either of the frequencies 3.14 MHz and 4.71 MHz.

Figure 4:
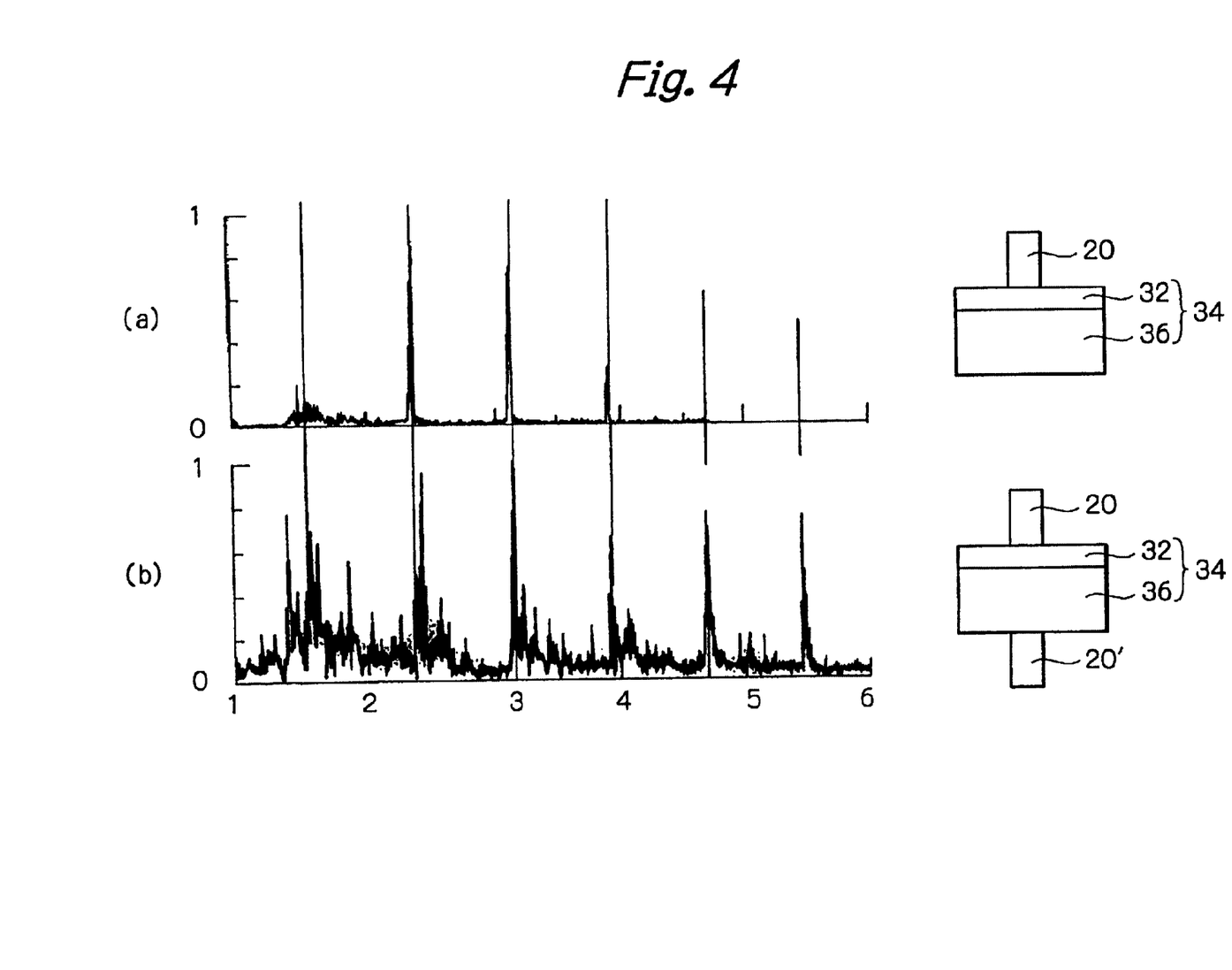
FIGS. 4a and 4b are graphs showing the amplitude of ultrasonic waves reflected and transmitted in a piled up structure 34 when the ultrasonic waves are applied to the piled up structure 34 from an EMAT 20.

FIGS. 4a and 4b are graphs showing the amplitude of ultrasonic waves reflected and transmitted in a piled up structure 34 comprising a first layer 32 and a second layer 36 when the ultrasonic waves are applied to the piled up structure 34 from an EMAT 20. In FIGS. 4a and 4b, the abscissa axis and the ordinate axis show the respective scales of the frequency and amplitude of ultrasonic waves. Ultrasonic waves in FIG. 4a are those received with an EMAT 20 disposed as shown in the right-hand part of FIG. 4a. The graph shows the measured values of ultrasonic waves reflected from the lower side of the piled up structure 34. Ultrasonic waves in FIG. 4b are those received with an EMAT 20' disposed as shown in the right-hand part of FIG. 4b. The graph shows the measured values of ultrasonic waves passing through the piled up structure 34 to the lower side thereof.

A comparison of the graph shown in FIG. 4a and the graph shown in FIG. 4b reveals that substantially similar measured values appear at specific frequencies. Accordingly, when ultrasonic waves are applied to the piled up structure 34 comprising the first layer 32 and the second layer 36 from the EMAT 20 disposed at the upper surface of the first layer, ultrasonic waves of specific frequencies pass through the first layer 32 and the second layer 36 and are reflected at the lower surface of the second layer 36. Thereafter, the reflected ultrasonic waves pass through the second layer and the first layer and are measured by the EMAT 20 at the upper surface of the first layer.

Figure 5:
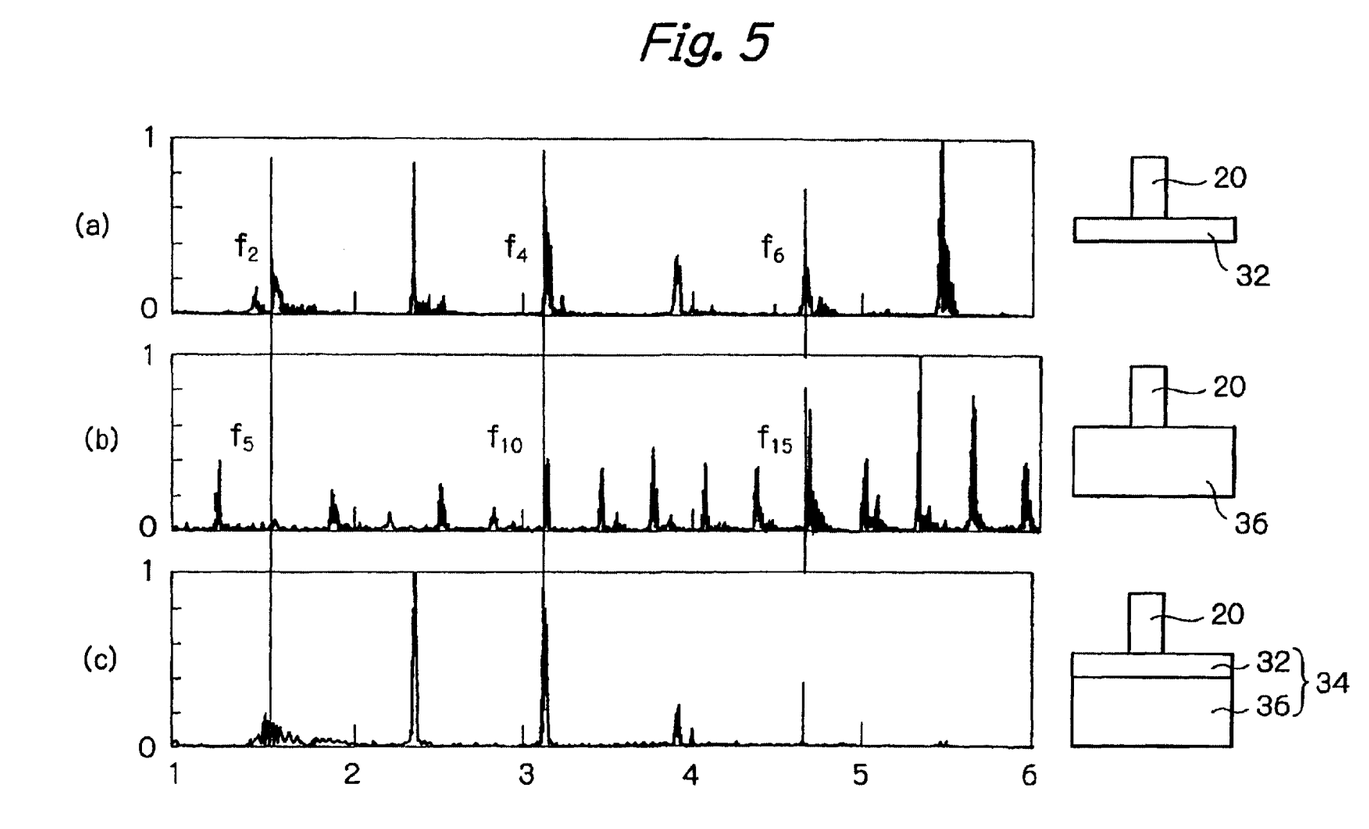
FIGS. 5a, 5b and 5c show frequencies (abscissa axes) fn (MHz) when the 1 st to 15 th resonant frequencies are applied to a first layer 32 of metal plate with a thickness of 2 mm, a second layer 36 of metal plate with a thickness of 5 mm, and a piled up structure 34 comprising the first and second layers riveted together, respectively, from an EMAT 20 disposed at the upper surface of each of the first layer 32, the second layer 36 and the piled up structure 34, together with the standardized values of amplitude A of ultrasonic waves reflected from the lower side of each of the first layer 32, the second layer 36 and the piled up structure 34.

FIGS. 5a, 5b and 5c show the relationship between, on the one hand, the frequencies (abscissa axes) fn (MHz) when the 1 st to 15 th resonant frequencies are applied to a first layer 32 of metal plate with a thickness of 2 mm, a second layer 36 of metal plate with a thickness of 5 mm, and a piled up structure 34 comprising the first and second layers riveted together from an EMAT 20 disposed at the upper surface of each of the first layer 32, the second layer 36 and the piled up structure 34, and, on the other, the standardized values of the amplitude A (standardized such that the maximum amplitude is expressed as 1; ordinate axis) of ultrasonic waves reflected from the lower side of each of the first layer 32, the second layer 36 and the piled up structure 34.

In FIGS. 5a, 5b and 5c, the 2 nd resonant frequency f2 (about 1.57 MHz), the 4 th resonant frequency f4 (about 3.14 MHz) and the 6 th resonant frequency f6 (about 4.71 MHz) of the first layer 32 are approximately coincident with the 5 th resonant frequency f5, the 10 th resonant frequency f10 and the 15 th resonant frequency f15, respectively, of the second layer 36. A comparison of FIGS. 5a, 5b and 5c reveals that the sum of the amplitude of the 4 th resonant frequency f4 (about 3.14 MHz) in the first layer 32 and the amplitude of the 10 th resonant frequency f10 (about 3.14 MHz) in the second layer 36 is coincident with the amplitude of the ultrasonic waves in the piled up structure 34 shown in FIG. 5c. Therefore, the condition of the material of the second layer can be diagnosed by using a resonant frequency common to the first and second layers as stated above.

Figure 6:
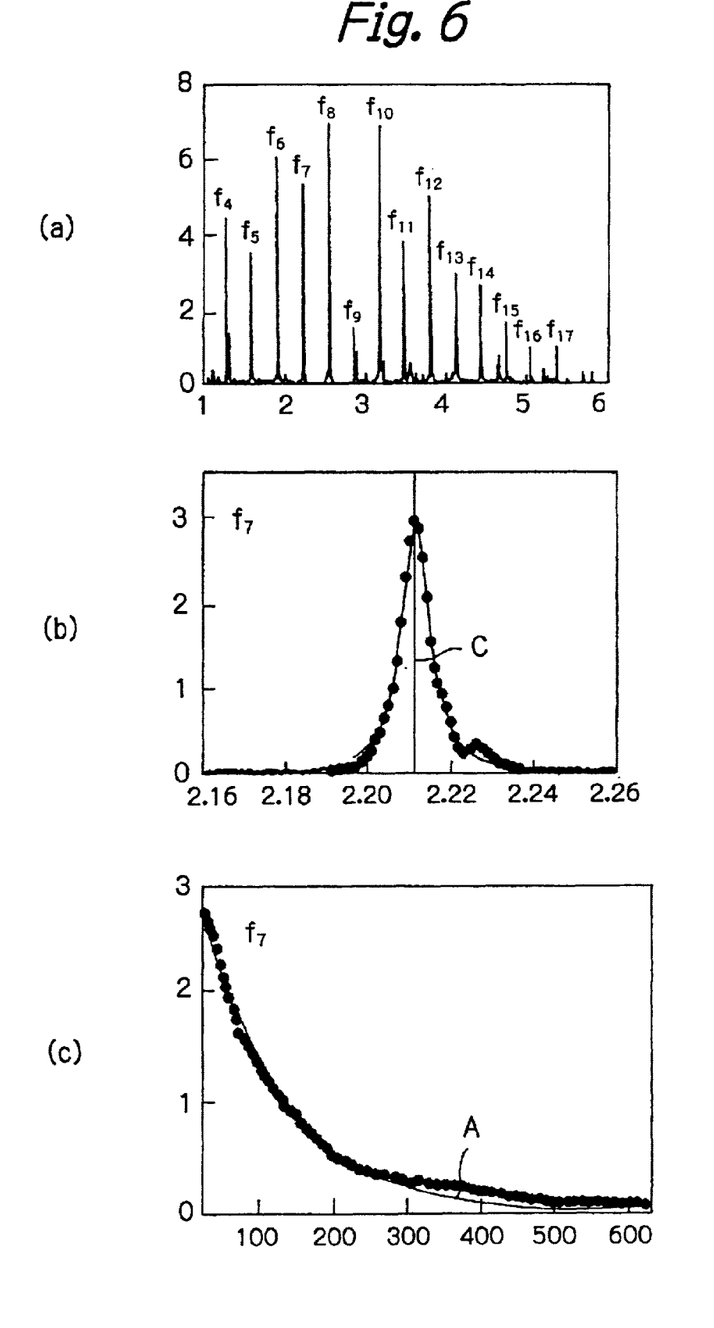
FIGS. 6a, 6b and 6c are graphs for explaining a method of measuring the attenuation of ultrasonic waves.

FIGS. 6a, 6b and 6c are graphs for explaining a method of measuring the attenuation of ultrasonic waves. The curve in the graph of FIG. 6a shows the relationship (resonant spectrum) between the radio-frequency burst current (abscissa axis; MHz) applied from an EMAT to a 304 stainless steel having a thickness of 5 mm and the amplitude of the detected ultrasonic waves (ordinate axis; a.u.). f1, f2, ... f17 are the orders of resonant mode. FIG. 6b is an enlarged view of the 7 th resonant mode f7 in the resonant spectrum shown in FIG. 6a. In the enlarged view of the 7 th resonant mode shown in FIG. 6b, the curve approximated to the measured values forms a crest between the frequencies of about 2.19 MHz and 2.23 MHz, and the center axis C of the crest curve, i.e. the frequency of the 7 th resonant mode, is at about 2.21 MHz.

FIG. 6c is a graph showing the ringdown curve A at the frequency (about 2.21 MHz) of the 7 th resonant mode, i.e. changes with time of the amplitude after the supply of the burst current has been stopped. Assuming that the measured values are approximated by the curve A of the above-described equation (2), the attenuation coefficient $\alpha$ is determined as $\alpha = 0.008$ m$\mu$/sec.

Figure 7:
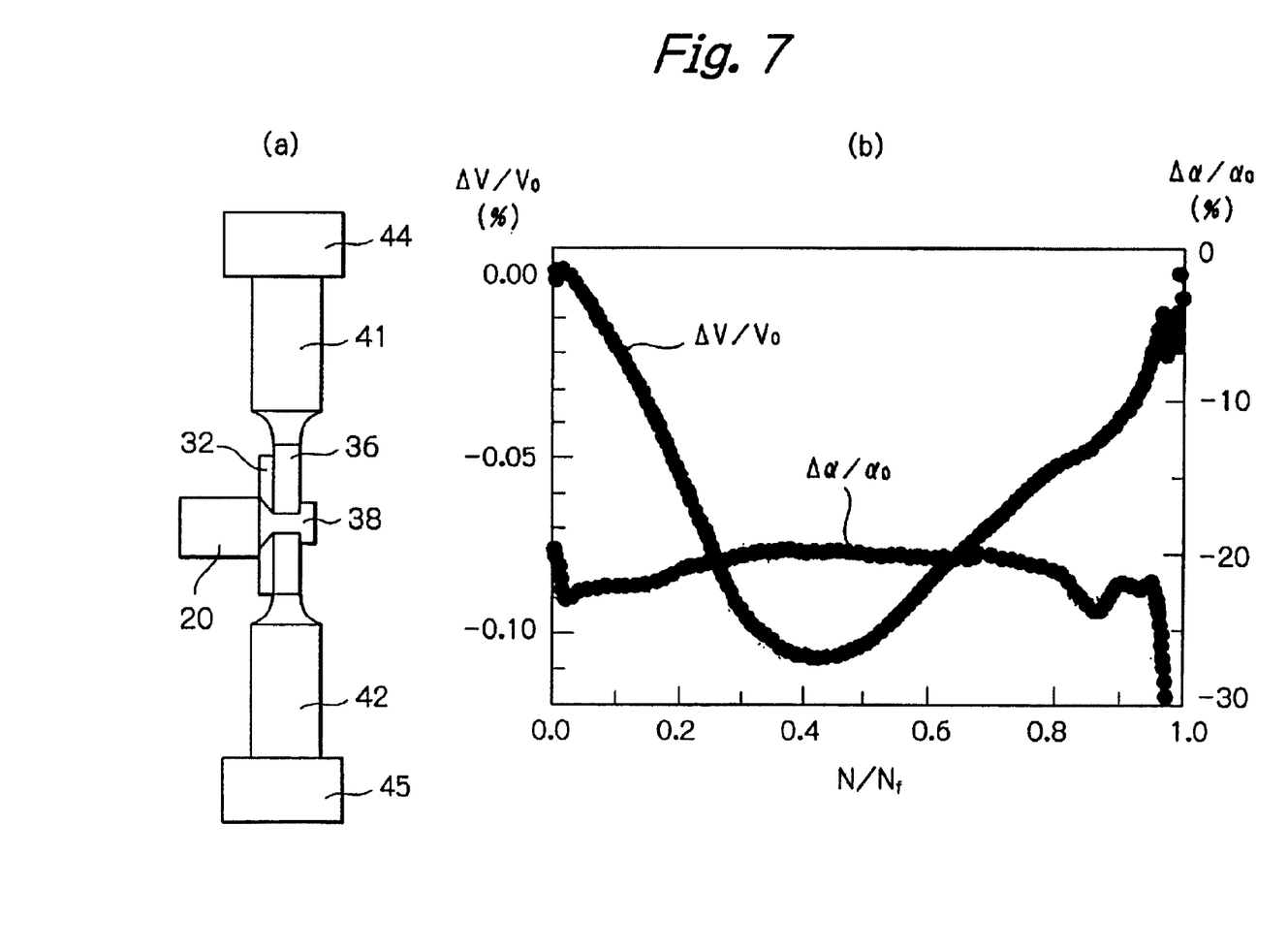

FIG. 7a is a diagram showing the arrangement of a testing apparatus for examining the fatigue of a material and changes in the attenuation coefficient and velocity of ultrasonic waves, which is used in the evaluation method of the present invention, and FIG. 7b is a graph of the changes in the attenuation coefficient and velocity obtained by using the testing apparatus shown in FIG. 7a. In the testing apparatus shown in FIG. 7a, an EMAT 20 is disposed adjacent to a first layer 32 of a piled up structure having a first layer 32 and a second layer 36 fastened together with a rivet 38 as an object to be measured. The second layer 36 is coupled to repeated load applying mechanisms 44 and 45 at extensions 41 and 42 thereof so that repeated load can be applied thereto.

In FIG. 7b, the abscissa axis shows the number of times of application of repeated load (normal stress: 55 MPa) to the second layer 36. In other words, the abscissa axis shows the ratio N/Nf of the cycle N of repeated loading to the cycle Nf (150,600 cycles) of repeated loading at which the second layer 36 fractures. FIG. 7b shows the velocity V and attenuation coefficient $\alpha$ of ultrasonic waves obtained from the piled up structure by the EMAT 20 using a frequency of about 3.1 MHz in the testing apparatus shown in FIG. 7a. In FIG. 7b, the velocity V of the ultrasonic waves is shown by the ratio $\Delta V/V0$ (%) of the velocity change $\Delta V$ to the velocity V0 in a stationary state. The scale thereof is shown along the left-hand ordinate axis. The attenuation coefficient $\alpha$ of the ultrasonic waves is shown by the ratio $\Delta\alpha/\alpha 0$ of the attenuation coefficient change $\Delta\alpha$ to the attenuation coefficient $\alpha 0$ (%) in a stationary state. The scale thereof is shown along the right-hand ordinate axis.

In FIG. 7b, the curve $\Delta\alpha/\alpha 0$ showing the attenuation coefficient gradually increases after decreasing rapidly and then decreases from a point (where N/Nf is about 0.81) at which a fatigue crack occurs. In FIG. 7b, the curve $\Delta V/V0$ showing the velocity of the ultrasonic waves assumes an approximately V shape, and the minimum value occurs where N/Nf is about 0.4.

Figure 8:
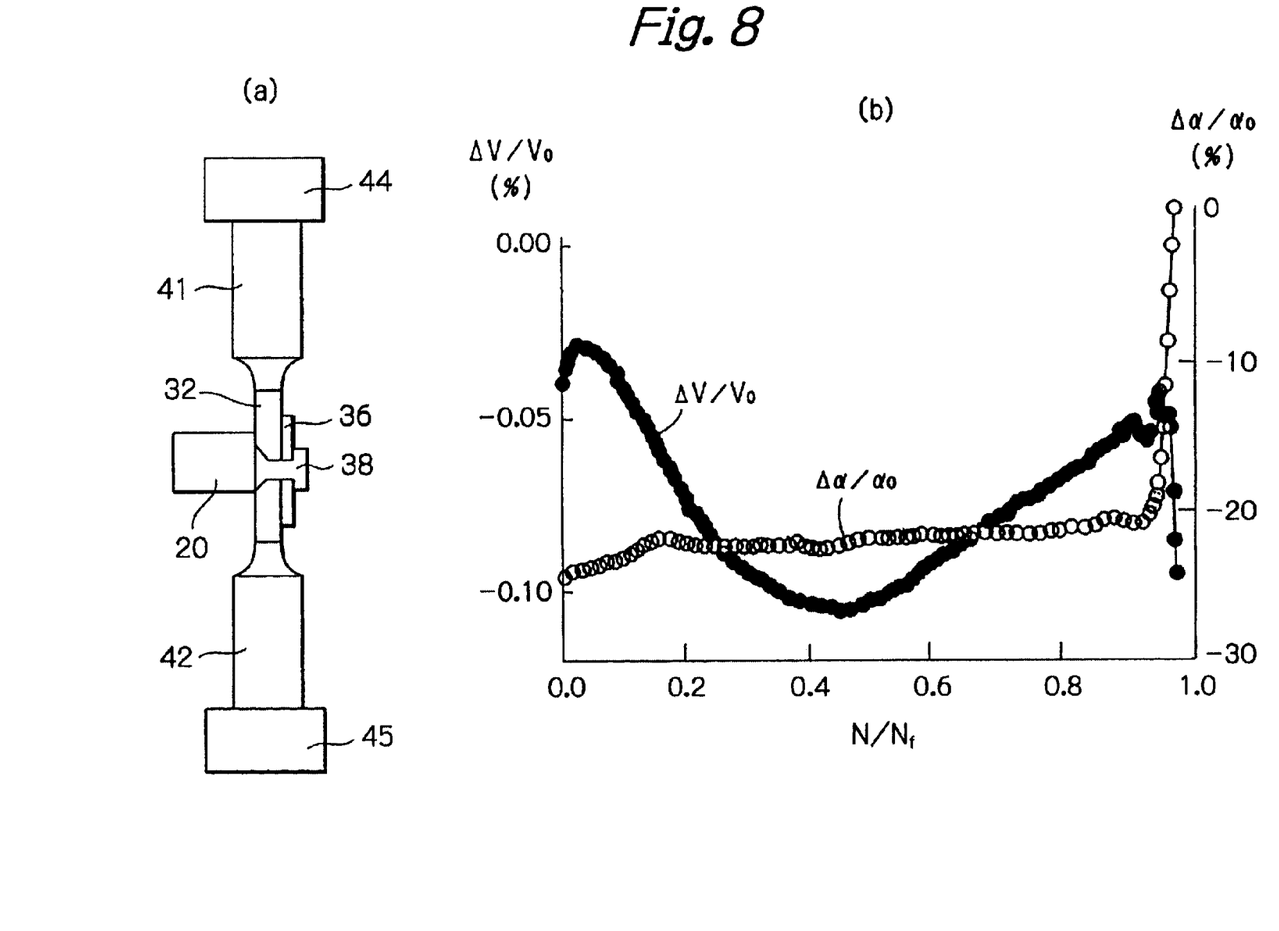

FIG. 8a is a diagram showing the arrangement of another testing apparatus for examining the fatigue of a material and changes in the attenuation coefficient and velocity of ultrasonic waves, which is used in the evaluation method of the present invention, and FIG. 8b is a graph of the changes in the attenuation coefficient and velocity obtained by using the testing apparatus shown in FIG. 8a. In the testing apparatus shown in FIG. 8a, an EMAT 20 is disposed adjacent to a first layer 32 of a piled up structure having a first layer 32 and a second layer 36 fastened together with a rivet 38 as an object to be measured. The first layer 32 is coupled to repeated load applying mechanisms 44 and 45 at extensions 51 and 52 thereof so that repeated load can be applied thereto.

In FIG. 8b, the abscissa axis shows the number of times of application of repeated load (normal stress: 47 MPa) to the first layer 32. In other words, the abscissa axis shows the ratio N/Nf of the cycle N of repeated loading to the cycle Nf (150,600 cycles) of repeated loading at which the first layer 32 fractures. FIG. 8b shows the velocity V and attenuation coefficient α of ultrasonic waves obtained from the piled up structure by the EMAT 20 using a frequency of about 3.1 MHz in the testing apparatus shown in FIG. 8a. In FIG. 8b, the velocity V of the ultrasonic waves is shown by the ratio ΔV/V0 (%) of the velocity change ΔV to the velocity V0 in a stationary state. The scale thereof is shown along the left-hand ordinate axis. The attenuation coefficient α of the ultrasonic waves is shown by the ratio Δα/α0 of the attenuation coefficient change Δα to the attenuation coefficient α0 (%) in a stationary state. The scale thereof is shown along the right-hand ordinate axis.

In FIG. 8b, the curve Δα/α0 showing the attenuation coefficient gradually increases and rapidly increases from a point (where N/Nf is about 0.81) at which a fatigue crack occurs. In FIG. 8b, the curve ΔV/V0 showing the velocity of the ultrasonic waves assumes an approximately V shape, and the minimum value occurs where N/Nf is about 0.4.

Figure 9:
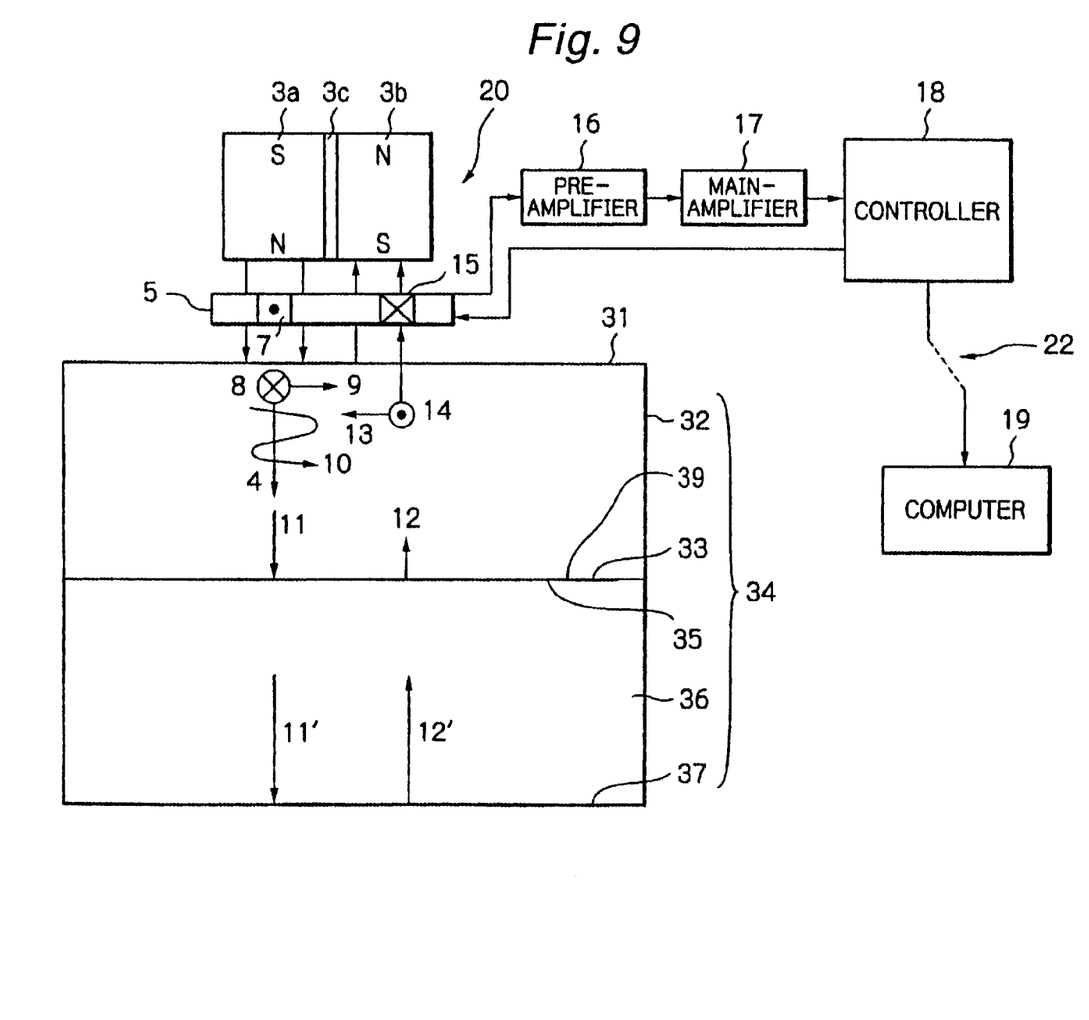
FIG. 9 is a diagram showing a diagnosing apparatus according to an embodiment of the present invention.

FIG. 9 is a diagram showing a diagnosing apparatus according to an embodiment of the present invention. Members similar to those in the diagram of FIG. 1 are denoted by the same reference numerals, and a redundant description thereof is omitted. As shown in FIG. 9, an EMAT 20 includes a pair of permanent magnets 3a and 3b disposed adjacent to the upper surface 31 of a piled up structure (object to be measured) 34 comprising a first layer 32 of a conductive material and a second layer 36 of a conductive material. The EMAT 20 further includes a driver coil 5 and a detection coil 15. The pair of permanent magnets 3a and 3b are placed adjacent to each other with a spacer 3c interposed therebetween. The permanent magnets 3a and 3b generate magnetic fields opposite in direction to each other with respect to the piled up structure 34. The permanent magnets 3a and 3b may be electromagnets arranged to generate similar magnetic fields. The driver coil 5 and the detection coil 15 are flat plate-shaped coils, which are disposed between the permanent magnets 3a and 3b on the one hand and the upper surface of the piled up structure 34 on the other.

The permanent magnets 3a and 3b form a static magnetic field 4 in the thickness direction of the piled up structure 34. When the driver coil 5 is supplied with a radio-frequency burst current 7 from a controller 18, an eddy current 8 is generated on the upper surface 31 of the piled up structure 34 in the direction reverse to that of the current 7. The eddy current 8 and the static magnetic field 4 interact each other to generate a Lorentz force 9 according to the Fleming's left-hand rule. The Lorentz force 9 acts on free electrons in the piled up structure 34, causing the free electrons to collide with ions and so forth, thereby inducing motions in a direction perpendicular to the directions of the static magnetic field 4 and the radio-frequency burst current 7 inside the piled up structure 34, and thus generating ultrasonic shear waves 10.

The ultrasonic shear waves 10 travel in the direction of the arrow 11 in FIG. 9. The ultrasonic shear waves 10 are reflected by the lower surface 33 of the first layer 32 of a conductive material and also reflected by flaws, defects, grain boundaries, changes of material's structure, etc. in the first layer 32 to travel in the direction of the arrow 12. Ultrasonic waves passing through the lower surface 33 of the first layer 32 of a conductive material, through a non-conductive interface 39 between the lower surface 33 and the upper surface 35 of the second layer 36, and through the upper surface 35 of the second layer 36 and traveling through the second layer 36 in the direction of the arrow 11' are reflected by the lower surface 37 of the second layer 36 and also reflected by flaws, defects, grain boundaries, changes of material's structure, etc. in the second layer 36 to travel in the direction of the arrow 12'.

When the reflected ultrasonic shear waves 10 reach the vicinity of the upper surface 31 of the piled up structure 34, a force 13 is generated. The force 13 and the static magnetic field 4 interact each other to generate an eddy current 14. The eddy current 14 is detected with the detection coil 15. The detected current is amplified by a pre-amplifier 16 and a main amplifier 17 and sent to the controller 18. The controller 18 analyzes the current received from the main amplifier 17 to evaluate flaws, defects, grain boundaries, changes of material's structure, etc. in the piled up structure 34. The computer part 19 of the controller 18 is disposed at a remote place, and the controller 18 and the computer part 19 are connected through a telecommunication mechanism 22.

The method and apparatus according to the present invention can make a non-contact diagnosis to evaluate damage to a piled up structure of conductive materials, e.g. fatigue, creep, corrosion, and stress crack. The present invention allows damage evaluation to be performed for the whole piled up structure in the thickness direction and for each layer of the piled up structure without the need to disassemble the piled up structure, and hence requires a reduced time and labor to make a diagnosis. It is also possible according to the present invention to evaluate a reduction in fastening force due to deterioration of or damage to fasteners, e.g. rivets or bolts, used to fasten together the layers of a piled up structure of conductive materials. Further, the present invention can evaluate damage before the occurrence of a crack due to the fatigue, creep, stress corrosion, etc. of the material. Therefore, it is possible to enhance the reliability of the piled up structure. In particular, it is possible to enhance the reliability of structures fastened with rivets, bolts, etc., such as airplanes, vessels, and bridges.

According to the method of the present invention, an electro-magnetic acoustic transducer is placed out of contact with a piled up structure to be measured. Therefore, the method has the advantage that measurement errors are favorably small even when the piled up structure has a non-smooth surface. The present invention further has the advantage that errors are also small in diagnosing a piled up structure forming bent portions, e.g. elbows. In the present invention, the computer part of the controller is disposed at a place separate or remote from the material to be measured, and the controller and the computer part are connected through a telecommunication mechanism. This arrangement allows diagnosis to be made to evaluate large piled up structures, e.g. airplanes, vessels, and bridges, in a non-contact manner at a separate or remote place and makes it possible to eliminate the inconvenience of having to install the computer near the piled up structure.

What is claimed is:

1. A method of diagnosing a condition of a piled up structure of conductive materials piled up with a non-conductive interface interposed therebetween and fastened together with a fastening member, said method comprising the steps of:

placing an electro-magnetic acoustic transducer out of contact with the piled up structure;

transmitting ultrasonic waves capable of passing through the non-conductive interface from one side of said piled up structure by said electro-magnetic acoustic transducer;

receiving ultrasonic waves reflected from the other side of the piled up structure by said electro-magnetic acoustic transducer; and diagnosing fastening force of the fastening member of said piled up structure on a basis of changes in an ultrasonic velocity and attenuation of the ultrasonic waves received.

2. A method according to claim 1, wherein the step of diagnosing is carried out by using computer software.

3. A method according to claim 1, wherein the step of diagnosing further includes the step of transmitting an electric signal to a place separate or remote from a part of the piled up structure to be diagnosed.

4. An apparatus for diagnosing a condition of a piled up structure of conductive materials piled up with a non-conductive interface interposed therebetween and fastened together with a fastening member, said apparatus comprising:

an electro-magnetic acoustic transducer placed out of contact with the piled up structure;

a controller for controlling an operation of the electro-magnetic acoustic transducer; and a computer for evaluating damage to the piled up structure on a basis of an electric signal obtained by the electro-magnetic acoustic transducer;

wherein said electro-magnetic acoustic transducer can transmit ultrasonic waves of a frequency capable of propagating through the non-conductive interface from one side of said piled up structure and can also receive ultrasonic waves reflected from the other side of the piled up structure, and said computer diagnoses fastening force of the fastening member of said piled up structure on a basis of an ultrasonic velocity and attenuation of the ultrasonic waves received.

5. An apparatus according to claim 4, further comprising a communication mechanism capable of teletransmission, said communication mechanism being capable of transmitting the electric signal obtained by the electro-magnetic acoustic transducer to the computer having diagnosing software.

* * * * *